(12) United States Patent
Carnali et al.

(10) Patent No.: US 8,241,614 B2
(45) Date of Patent: Aug. 14, 2012

(54) COMPOSITIONS AND METHODS FOR IMPARTING A SUNLESS TAN

(75) Inventors: Joseph Oreste Carnali, Newtown, CT (US); Qiang Qiu, Trumbull, CT (US); Xi Yuan Hua, Jersey City, NJ (US)

(73) Assignee: Conopco, Inc, Englewood Cliffs, NJ (US)

( * ) Notice: Subject to any disclaimer, the term of this patent is extended or adjusted under 35 U.S.C. 154(b) by 409 days.

(21) Appl. No.: 12/627,566

(22) Filed: Nov. 30, 2009

(65) Prior Publication Data

US 2011/0129427 A1 Jun. 2, 2011

(51) Int. Cl.
*A61Q 11/00* (2006.01)
*A61Q 17/04* (2006.01)
*A61K 8/18* (2006.01)

(52) U.S. Cl. ........................................................ 424/59
(58) Field of Classification Search ....................... 424/59
See application file for complete search history.

(56) References Cited

U.S. PATENT DOCUMENTS

| | | | |
|---|---|---|---|
| 4,405,616 A | 9/1983 | Rajadhyaksha | 424/244 |
| 4,886,783 A | 12/1989 | Minaskanian et al. | 574/29 |
| 5,118,845 A | 6/1992 | Peck et al. | 564/215 |
| 5,232,688 A | 8/1993 | Ziegler et al. | 424/59 |
| 5,612,044 A | 3/1997 | Suares et al. | 424/401 |
| 5,645,822 A | 7/1997 | Meyer et al. | 424/59 |
| 5,720,948 A | 2/1998 | Brucks et al. | 424/78.02 |
| 5,750,092 A | 5/1998 | Meyer et al. | 424/59 |
| 5,756,075 A | 5/1998 | Meyer | 424/59 |
| 6,231,837 B1 | 5/2001 | Stroud et al. | 424/59 |
| 2005/0089486 A1 | 4/2005 | Spindler et al. | 424/59 |
| 2009/0155321 A1 | 6/2009 | Harichian et al. | 424/401 |

FOREIGN PATENT DOCUMENTS

WO 97/33560 9/1997

OTHER PUBLICATIONS

Co-pending Application: Applicant: Carnali et al., U.S. Appl. No. 12/909,874, filed Oct. 22, 2010.
Co-pending Application: Applicant: Lou et al., U.S. Appl. No. 12/855,348, filed Aug. 12, 2010.
Co-pending Application: Applicant: Lou; U.S. Appl. No. 12/784,046, filed May 20, 2010.

*Primary Examiner* — Sreeni Padmanabhan
*Assistant Examiner* — Luke Karpinski
(74) *Attorney, Agent, or Firm* — Edward A. Squillante, Jr.

(57) ABSTRACT

A composition and method for imparting a sunless tan to skin is described. The composition and method make use of a sunless tanning agent like dihydroxyacetone in combination with an adjuvant such as a phosphorylated peptide.

14 Claims, No Drawings

COMPOSITIONS AND METHODS FOR IMPARTING A SUNLESS TAN

FIELD OF THE INVENTION

The present invention is directed to a composition and method for imparting a sunless tan to skin. More particularly, the invention is directed to a composition and method that employ a sunless tanning agent as well as an adjuvant for the sunless tanning agent. The composition, when applied, unexpectedly results in the consumer having skin with a brownish/tan coloration within a consumer acceptable time and surprisingly does not prematurely result in color bodies as rapidly as compositions formulated with glycine as an adjuvant.

BACKGROUND OF THE INVENTION

Sunless tanning agents are formulated into two types of cosmetic products. Of these, the most traditional is the self-tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Most prominent among the sunless tanning agents is dihydroxyacetone ("DHA" which is also chemically known as 1,3-dihydroxy-2-propanone). DHA, after application, is believed to exert its effect through interactions between its hydroxyl groups and the amino groups of amino acids and peptides naturally occurring in the hydrolipid pellicle and first layers of the stratum corneum of the skin. These so-called Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Unfortunately, many sunless tanning products available on the market are not stable in that they turn a yellow and/or orange color after application, especially when exposed to UV light. Other sunless tanning products perform poorly and do not quickly impart a noticeable brown color after application. Such poorly performing products do not prevent "tan-happy" consumers from basking in the sun. Products that underperform, therefore, do not protect consumers from the sun's ultraviolet rays.

There is increasing interest to develop compositions and methods for imparting a sunless tan, and especially, compositions that are storage stable. This invention, therefore, is directed to a composition and method that employ a sunless tanning agent as well as an adjuvant for the sunless tanning agent. The composition, when applied, unexpectedly results in the consumer having skin with a brownish/tan coloration within a consumer acceptable time and, surprisingly, does not turn orange and/or yellow prior or after use and when exposed to ultraviolet light.

Additional Information

Efforts have been disclosed for making self-tanning cosmetic compositions. In U.S. Pat. Nos. 5,232,688 and 5,612,044, self-tanner compositions with DHA are described.

Other efforts have been disclosed for making self-tanning compositions. In U.S. Pat. No. 5,750,092, compositions with DHA and secondary amines are described.

Still other efforts have been disclosed for making self-tanning compositions. In U.S. Pat. No. 6,231,837, self tanning formulations comprising DHA, polyethoxyglycol and a polyol are described.

None of the additional information describes a method and/or composition that yield excellent sunless tanning results whereby the composition and method employ a sunless tanning agent and a phosphorylated peptide.

SUMMARY OF THE INVENTION

In a first aspect, the present invention is directed to a composition comprising:
 a) a sunless tanning agent; and
 b) an adjuvant for the sunless tanning agent, the adjuvant being a phosphorylated peptide.

In a second aspect, the present invention is directed to a method for generating a sunless tan comprising the step of applying to the skin the composition of the first aspect of this invention.

All other aspects of the present invention will more readily become apparent upon considering the detailed description and examples which follow.

Sunless tanning, as used herein, means obtaining the suntan look by applying a topical composition. The same can be interchanged with self-tanning. Composition, as used herein, is meant to include a substance applied to a human body for imparting a sunless tan where the composition is for example, a leave-on skin lotion, cream or mouse, shampoo, hair conditioner, shower gel, toilet bar, body wash, shaving cream, body wax, depilatory, mascara, sunscreen product or the like. Such a composition may also be put on body towelettes for application to the body. In a preferred embodiment, the composition of this invention is a lotion or cream. Consumer acceptable time means within about 3 to about 6 hours from application, and preferably, from about 1 to about 2 hours, and most preferably, from about 15 to about 30 minutes subsequent to application. A composition not rapidly resulting in color bodies prematurely means being storage stable where storage stable is defined to mean having an optical absorbance at 500 nm of less than about 7 (as determined with a spectrophotometer) when stored at 50° C. for about 138 hours at a pH of about 4.5 (corresponding to a delta absorbance/delta time, $hr^{-1}$ as shown in the Examples).

Comprising, as used herein, is meant to include consisting essentially of and consisting of. All ranges identified herein are meant to include all ranges subsumed therein if, for example, reference to the same is not explicitly made.

DETAILED DESCRIPTION OF THE INVENTION

The sunless tanning agent suitable for use in this invention is only limited to the extent that it may be applied topically on humans to form pigmented components. Such materials may be alpha-hydroxyaldelydes and ketones, glyceraldehyde, troxerutin and related alcohol aldehydes, various indoles, imidazoles and derivatives thereof.

Illustrative yet non-limiting examples of the sunless tanning agents that may be used in this invention include dihydroxyacetone, melanin, mahakanni (eclipta alba), methyl glyoxal, erythrulose, alloxan, 2,3-dihydroxysuccindialdehyde, mixtures thereof, or the like. In a preferred embodiment, the sunless tanning agent used is dihydroxyacetone, erythrulose or a mixture thereof. In a most preferred embodiment, the sunless tanning agent is dihydroxyacetone.

Typically, the sunless tanning agent makes up from about 0.025 to about 35%, and preferably, from about 0.05 to about 15%, and most preferably, from about 0.5 to about 10% by weight of the composition, based on total weight of the composition and including all ranges subsumed therein.

The adjuvant (i.e., phosphorylated peptide) that may be used in this invention is limited only to the extent that the same may be used in a composition suitable for topical application to humans.

Typically, the phosphorylated peptide has the formula:

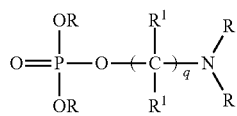

where each R is independently hydrogen, $C_{1-8}$ alkyl, $C_{4-8}$ cycloalkyl, or aryl;
each $R^1$ is independently

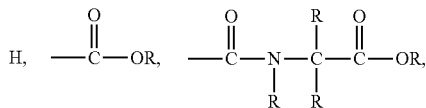

$C_{1-8}$ alkyl, $C_{4-8}$ cycloalkyl or aryl;
and q is an integer from about 1 to about 8.

In a most preferred embodiment, the sunless tanning adjuvant used in this invention is o-phosphorylethanolamine. Typically, the adjuvant makes up from about 0.025 to about 35%, and preferably, from about 0.05 to about 15%, and most preferably, from about 0.5 to about 8% by weight of the composition, including all ranges subsumed therein.

Compositions of the present invention will typically include a cosmetically acceptable carrier. Water is the most preferred carrier. Amounts of water may range from about 1 to about 99%, and preferably, from about 5 to about 90%, and most preferably, from about 35 to about 80% and optimally from about 40 to about 75% by weight, based on total weight of the composition and including all ranges subsumed therein. Ordinarily the compositions will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the actives and adjuvants of this invention described in commonly owned U.S. Patent Application Publication Nos. 2008/0311058 and 2009/0247445, the disclosures of which are incorporated herein by reference.

Other cosmetically acceptable carriers may include mineral oils, silicone oils, synthetic or natural esters, fatty acids and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities less than about 5 centistokes at 25° C. while cyclic materials typically have viscosities of less than about 10 centistokes.

Nonvolatile silicone oils useful as carrier material include nonvolatile polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isonanonoate, coleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;
(4) Wax esters such as beeswax, spermaceti, myristyl myristate, stearyl stearate; and
(5) Sterol esters, of which soya sterol and cholesterol fatty acid esters are examples thereof.

Fatty acids having from 10 to 30 carbon atoms may be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Emulsifiers may be present in the compositions of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions comprising the sunless tanning agent and adjuvant of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer.

Amounts of the thickener may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra (hydroxymethyl) urea; tetra(hydroxyethyl) urea; tetra (hydroxypropyl) urea; N-methyl-N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the composition and including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 50%, preferably between 1 and 15% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the end use composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the end use composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Conventional buffers/pH modifiers may be used. These include commonly employed additives like sodium hydroxide, hydrochloric acid, citric acid and citrate/citric acid buffers. In an especially preferred embodiment, the pH of the composition of this invention is from about 3 to about 4.75, and preferably, from about 3.25 to about 4, and most preferably, from about 3.25 to about 3.75, including all ranges subsumed therein.

Colorants, opacifiers, chelators (like tetrasodium EDTA) and abrasives may also be included in the compositions of the present invention. Each of these substances may range from about 0.05 to about 5%, preferably between 0.1 and 3% by weight of the composition.

In an especially preferred embodiment, the composition of the present invention comprises less than about 5%, and preferably, from 0.01 to 4% glycine, and most preferably, no glycine.

A wide variety of packaging can be employed to store and deliver the compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

Optionally, the composition of this invention may be divided so that a first portion may carry sunless tanning agent and a second portion may carry adjuvant. When dividing the composition, each portion should be packaged separately from each other and not come into contact with each other until application to the body. The packaging for dual compositions is known and commercially available. Upon application, the make up of the composition (i.e., the combined portions) is as described herein.

When making the composition of the present invention, ingredients may be combined in no particular order. Typically the ingredients are combined and mixed under conditions of moderate shear and at ambient temperature with pressure being atmospheric conditions. In a most preferred embodiment, DHA and adjuvant are not added at a time when mixing and heating are desired. When applied by the consumer, typically from about 1 to 5 mg, and preferably, from about 1 to 4 mg, and preferably, from about 1.5 to 2.5 mg per square centimeter of composition is applied to body surface (like skin) and including all ranges subsumed therein.

The following examples are provided to facilitate an understanding of the present invention. The examples are not intended to limit the scope of the claims.

Example 1

The following compositions were made by combining and mixing the ingredients identified below. Compositions with o-phosphorylethanolamine (OPEA) were made consistent with this invention. All other samples were comparative.

| Ingredients | Sample No. | | | | | | | | | |
|---|---|---|---|---|---|---|---|---|---|---|
| (weight %) | 1 | 2 | 3 | 4 | 5 | 6 | 7 | 8 | 9 | 10 |
| DHA | 2.5 | 2.5 | 2.5 | 2.5 | 2.5 | 2.5 | 2.5 | 2.5 | 2.5 | 2.5 |
| Glycerine | 12.5 | 12.5 | 12.5 | 12.5 | 12.5 | 12.5 | 12.5 | 12.5 | 12.5 | 12.5 |
| OPEA | 0 | 0 | 0 | 0 | 0 | 0 | 1 | 1 | 1 | 1.9 |
| Glycine | 0 | 0 | 0 | 1 | 1 | 1 | 0 | 0 | 0 | 0 |
| Buffer solution* | Balance | Balance | Balance | Balance | Balance | Balance | Balance | Balance | Balance | Balance |
| pH | 3.5 | 4.5 | 5.5 | 3.5 | 4.5 | 5.5 | 3.5 | 4.5 | 5.5 | 4.5 |

*(Buffer Maker, Version 1.0.1.55, © BPP Marcin Borkowski, 2008/9).

Samples 1 and 4 are comparative and sample 7 were made consistent with this invention. These samples were stored at 35° C. for 384 hours, where the turbidity of the same was monitored using a Carey Spectrophotometer operating at 500 nm. The results indicate that comparative composition 1 did not change color with DHA alone but comparative composition 4 did have a color change (about 0.03) when glycine was used as the DHA adjuvant. Sample 7 showed no color change under the aforementioned conditions, and therefore, surprisingly showed DHA and phosphorylated peptide adjuvants are storage stable at the aforementioned conditions, especially when compared to compositions with glycine.

Example 2

Comparative samples 1-3 as made in Example 1 were stored at 50° C. for 138 hours, where turbidity of the same was monitored using a Carey Spectrophotometer operating at conditions as described in Example 1. Results indicate that DHA alone displayed a color change of about 0.05 at a composition pH of 5.5. The results show the color activity of DHA in the absence of adjuvant.

Example 3

Optical absorbance at 500 nm for samples of DHA and either OPEA or glycine was observed. Temperature was set at 50° C. and samples were stored as indicated below. Sample numbers correspond to the samples made in Example 1 with pH set at 3.5.

| | Hours | | | | |
|---|---|---|---|---|---|
| Sample | 18 | 26 | 43 | 66 | 138 |
| 1 | 0 | 0 | 0 | 0 | 0 |
| 4 | 0.03 | 0.03 | 0.07 | 0.19 | 1.40 |
| 7 | 0 | 0 | 0 | 0.02 | 0.09 |

The results indicate that the use of OPEA (Sample 7) in lieu of glycine (Sample 4) results in a significantly more stable composition comprising DHA when the composition is at a pH of 3.5.

Example 4

Optical absorbance at 500 nm for samples of DHA and either OPEA or glycine was observed. Temperature was set at 50° C. and samples were stored as indicated below. Sample numbers correspond to the samples made in Example 1 with pH set at 4.5.

| | Hours | | | | |
|---|---|---|---|---|---|
| Sample | 18 | 26 | 43 | 66 | 138 |
| 2 | 0 | 0 | 0 | 0 | 0 |
| 5 | 0.19 | 0.37 | 1.02 | 2.00 | 10 |
| 8 | 0.07 | 0.12 | 0.36 | 0.83 | 2.60 |

The results indicate that the use of OPEA (Sample 8) in lieu of glycine (Sample 5) results in a significantly more stable adjuvant containing composition comprising DHA when the composition is at a pH of 4.5.

Example 5

Optical absorbance at 500 nm for samples of DHA and either OPEA or glycine was observed. Temperature was set at 50° C. and samples were stored as indicated below. Sample numbers correspond to the samples made in Example 1 with pH set at 5.5

| | Hours | | | | |
|---|---|---|---|---|---|
| Sample | 18 | 26 | 43 | 66 | 138 |
| 3 | 0 | 0 | 0 | 0.01 | 0.05 |
| 6 | 1.75 | 2.46 | 4.33 | 10 | 10 |
| 9 | 0.87 | 1.26 | 2.20 | 3.31 | 10 |

At a pH of 5.5, stability is an issue for DHA and an adjuvant at 50° C. Nevertheless, substitution of OPEA for glycine unexpectedly results in a measurable improvement in chemical stability when comparing both adjuvants.

Example 6

Chemical stability of DHA was assessed in the presence of OPEA and glycine at a mole ratio of adjuvant to DHA of 0.46. Color development was followed at 600 nm for the samples reported below and made as described in Example 1. Sample pH was 4.5 and temperature was set at 50° C. The measured absorbance was 2 to 3 times higher when glycine was used as the adjuvant in lieu of OPEA.

| | Hours | | | |
|---|---|---|---|---|
| Sample | 17 | 24 | 41 | 112 |
| 5 | 0.04 | 0.09 | 0.22 | 0.98 |
| 10 | 0.01 | 0.03 | 0.08 | 0.44 |

The data surprisingly reveals that the generation of color bodies is significantly slower when DHA is stored with OPEA instead of glycine as the adjuvant.

Example 7

The following compositions were made by combining and mixing the ingredients identified below. Compositions with o-phosphorylethanolamine were made consistent with this invention. All other samples are comparative. The buffer solution used was identical to the one used in Example 1.

| Ingredient | Sample | | | | | |
|---|---|---|---|---|---|---|
| (weight %) | 11 | 12 | 13 | 14 | 15 | 16 |
| DHA | 2.5 | 2.5 | 2.5 | 2.5 | 2.5 | 2.5 |
| OPEA | 0 | 0 | 0 | 1 | 1.9 | 2.5 |
| Glycine | 0 | 1 | 2.5 | 0 | 0 | 0 |
| Buffer solution | Balance | Balance | Balance | Balance | Balance | Balance |
| pH | 5.3 | 5.3 | 5.3 | 5.3 | 5.3 | 5.3 |

Color development capability of the above samples was assessed by using VITRO-SKIN® made commercially available by IMS, Inc. Such artificial substrate, which mimics the surface properties of human skin, was hydrated prior to using by storing the same for 24 hours in a desiccator containing a 15% glycerol-in-water solution, relative humidity 95%. The substrate was cut into squares (about 6 cm$^2$). Sample was applied (about 25 microliters) and evenly spread onto a circular area (about 5 cm$^2$) on the substrate. The substrate with sample was stored in a second desiccator charged with an equimolor mixture of glycerol and water at 35° C., relative humidity 40%. Color developed on the substrate and was monitored as a function of time using a HunterLab Labscan XE Colorimeter. L* coordinates (i.e., darkness or lightness of a color on an achromatic basis) were observed over a course of time.

The results obtained show that samples with OPEA gave color enhancement comparable to samples with equal weight of glycine. Maximum color development with DHA alone was reached in about 15 hours, but this level of color was exceeded in 2 hours when OPEA or glycine was formulated with DHA.

The ultimate darkening of the samples was assessed. Samples with DHA and OPEA were about 20% darker than samples with comparable amounts of DHA and glycine.

The results indicate that OPEA, which was shown to result in a DHA comprising composition which is more stable than a DHA comprising composition with glycine, yields a darker sunless tan with DHA than glycine does with DHA.

Example 8

The following compositions were made by combining and mixing the ingredients identified below. Compositions made with o-phosphorylethanolamine were made consistent with this invention. All other samples are comparative. The buffer solution used was identical to the one used in Example 1.

| Ingredient | Sample | | | | |
|---|---|---|---|---|---|
| (weight %) | 17 | 18 | 19 | 20 | 21 |
| DHA | 2.5 | 2.5 | 2.5 | 2.5 | 2.5 |
| Glycerin | 0 | 12.5 | 0 | 0 | 0 |
| Propylene glycol | 0 | 0 | 12.5 | 0 | 0 |
| Dipropylene glycol | 0 | 0 | 0 | 12.5 | 0 |
| Butylene glycol | 0 | 0 | 0 | 0 | 12.5 |
| OPEA | 1 | 1 | 1 | 1 | 1 |
| Buffer solution | Balance | Balance | Balance | Balance | Balance |
| pH | 4.5 | 4.5 | 4.5 | 4.5 | 4.5 |

The chemical storage stability of DHA in the above samples was gauged by measuring optical density (with a spectrophotometer set at 500 nm) developed upon storage of the samples at pH 4.5 and 50° C. for a period which extended up to 100 hours. The results of the measurements assessed are reported as slope of absorbance versus time plot.

| Sample | Δ absorbance (at 500 nm)/Δ time, hr$^{-1}$ |
|---|---|
| 17 | 0.018 |
| 18 | 0.018 |
| 19 | 0.019 |
| 20 | 0.027 |
| 21 | 0.026 |

At a 12.5% polyol level, the presence of glycerin (Sample 18) or propylene glycol (Sample 19) does not adversely affect the stability of DHA plus OPEA relative to the control (Sample 17). However, dipropylene glycol (Sample 20) and butylene glycol (Sample 21) both reduced the chemical stability of DHA.

Example 9

The following compositions were made by combining and mixing the ingredients identified below. Compositions with o-phosphorylethanolamine were made consistent with this invention. All other samples were comparative. The buffer solution used was identical to the one used in Example 1.

| Ingredient | Sample | | | | | | |
|---|---|---|---|---|---|---|---|
| (weight %) | 22 | 23 | 24 | 25 | 26 | 27 | 28 |
| DHA | 2.5 | 2.5 | 2.5 | 2.5 | 2.5 | 2.5 | 2.5 |
| Glycerin | 0 | 25 | 0 | 0 | 0 | 0 | 0 |
| Diethylene glycol | 0 | 0 | 25 | 0 | 0 | 0 | 0 |
| Triethylene glycol | 0 | 0 | 0 | 25 | 0 | 0 | 0 |
| Tetraethylene glycol | 0 | 0 | 0 | 0 | 25 | 0 | 0 |
| Propylene glycol | 0 | 0 | 0 | 0 | 0 | 25 | 0 |
| Dipropylene glycol | 0 | 0 | 0 | 0 | 0 | 0 | 25 |
| OPEA | 1 | 1 | 1 | 1 | 1 | 1 | 1 |
| Buffer solution | Balance | Balance | Balance | Balance | Balance | Balance | Balance |
| pH | 4.5 | 4.5 | 4.5 | 4.5 | 4.5 | 4.5 | 4.5 |

The chemical storage stability of DHA in the above samples was gauged by measuring optical density (with a spectrophotometer set at 500 nm) developed upon storage of the samples at pH 4.5 and 50° C. for a period up to 100 hours. Results of the measurements are reported as the slope of absorbance versus time plot.

| Sample | Δ absorbance (at 500 nm)/Δ time, hr$^{-1}$ |
|---|---|
| 22 | 0.016 |
| 23 | 0.018 |
| 24 | 0.031 |
| 25 | 0.024 |
| 26 | 0.026 |
| 27 | 0.018 |
| 28 | 0.028 |

At a 25% polyol level, the presence of glycerin (Sample 23) or propylene glycol (Sample 27) does not affect the chemical stability of DHA and OPEA relative to the control (Sample 22). All other glycols tested did, to a degree reduce the stability of DHA.

Example 10

The following compositions were made by combining and mixing the ingredients identified below. Compositions with o-phosphorylethanolamine were made consistent with this invention. All other samples were comparative. The buffer solution used was identical to the one used in Example 1.

| Ingredient | Sample | | | | | | | | |
|---|---|---|---|---|---|---|---|---|---|
| | 29 | 30 | 31 | 32 | 33 | 34 | 35 | 36 | 37 |
| DHA | 2.5 | 2.5 | 2.5 | 2.5 | 2.5 | 2.5 | 2.5 | 2.5 | 2.5 |
| Glycerin | 0 | 50 | 0 | 0 | 0 | 0 | 0 | 0 | 0 |
| Diethylene glycol | 0 | 0 | 50 | 0 | 0 | 0 | 0 | 0 | 0 |
| Triethylene glycol | 0 | 0 | 0 | 50 | 0 | 0 | 0 | 0 | 0 |
| Tetraethylene glycol | 0 | 0 | 0 | 0 | 50 | 0 | 0 | 0 | 0 |
| Propylene glycol | 0 | 0 | 0 | 0 | 0 | 50 | 0 | 0 | 0 |
| Dipropylene glycol | 0 | 0 | 0 | 0 | 0 | 0 | 50 | 0 | 0 |
| Butylene glycol | 0 | 0 | 0 | 0 | 0 | 0 | 0 | 50 | 0 |
| Isosorbid diethylether | 0 | 0 | 0 | 0 | 0 | 0 | 0 | 0 | 50 |
| OPEA | 1 | 1 | 1 | 1 | 1 | 1 | 1 | 1 | 1 |
| Buffer solution at pH | balance 4.5 | balance 4.5 | balance 4.5 | balance 4.5 | balance 4.5 | balance 4.5 | balance 4.5 | balance 4.5 | balance 4.5 |

The chemical storage stability of DHA in the above samples was gauged by measuring the optical density (with a spectrophotometer set at 500 nm) developed upon storage of the samples at pH 4.5 and 50° C. for a period up to 100 hours. Results of the measurements are reported as the slope of absorbance versus time plot.

| Sample | Δ absorbance (at 500 nm)/Δ time, hr $^{-1}$ |
|---|---|
| 29 | 0.016 |
| 30 | 0.022 |
| 31 | 0.092 |
| 32 | 0.086 |
| 33 | 0.083 |
| 34 | 0.026 |
| 35 | 0.088 |
| 36 | 0.092 |
| 37 | 0.083 |

At a 50% polyol level, the presence of glycerin (Sample 30) or propylene glycol (Sample 34) only slightly affected the stability of DHA and OPEA relative to the control (Sample 29). Excluding the glycols used at the levels in samples 31-33 and 35-37, all other glycols used resulted in a storage stable composition as defined herein and under the aforementioned conditions.

Example 11

The following ingredients were combined to prepare illustrative compositions. Moderate shear was used under atmospheric conditions. The contents were heated to about 65° C. and cooled. Composition pH was maintained at 3.5. DHA and OPEA were added with stirring after the contents cooled.

| Ingredient | % w/w Sample 38 |
|---|---|
| Hydroxyethyl acrylate/sodium acryloyldimethyl taurates copolymer/squalane polysorbate 60 | 1.5 |
| Thickener | 0.10 |
| Chelator | 0.11 |
| Preservative | 0.3 |
| Glycerin | 12.0 |
| Citric acid | 0.1-0.2 |
| Colorant | 0.19 |
| Stearic acid | 1.97 |
| Glycol stearate/steramide AMP | 1.17 |
| Glyceryl stearate | 0.55 |
| PEG 100 stearate | 1.0 |
| Cetyl alcohol | 0.31 |
| Isopropyl palmitate | 2.25 |
| Dimethicone | 1.0 |
| Cyclopentasiloxane/dimethiconol | 0.4 |
| Fixative | 0.4 |
| Fragrance | 0.35 |
| DHA | 2.5 |
| OPEA | 1.0 |
| Deionized water | to 100 |

Example 12

The following compositions (pH about 3.5) were made by mixing the following ingredients in the manner described in Example 11. Erythrulose and alloxan were added with DHA.

| Ingredient | % w/w (Sample 39) | % w/w (Sample 40) |
|---|---|---|
| Hydroxyethyl acrylate/sodium acryloyldimethyl taurates copolymer/squalane polysorbate 60 | 1.5 | 1.5 |
| Thickener | 0.10 | 0.10 |
| Chelator | 0.11 | 0.11 |
| Preservative | 0.12 | 0.12 |
| Glycerin | 12.0 | 12.0 |
| Citric acid | 0.1-0.2 | 0.1-0.2 |
| Colorant | 0.19 | 0.19 |
| Stearic acid | 1.97 | 1.97 |
| Glycol stearate/steramide AMP | 1.17 | 1.17 |
| Glyceryl stearate | 0.55 | 0.55 |
| PEG 100 stearate | 1.0 | 1.0 |
| Cetyl alcohol | 0.31 | 0.31 |
| Isopropyl palmitate | 2.25 | 2.25 |
| Dimethicone | 1.0 | 1.0 |
| Cyclopentasiloxane/dimethiconol | 0.50 | 0.5 |
| Fixative | 0.4 | 0.4 |
| Fragrance | 0.35 | 0.35 |
| DHA | 2.0 | 2.0 |
| Erythrulose | 0.5 | — |

-continued

| Ingredient | % w/w (Sample 39) | % w/w (Sample 40) |
|---|---|---|
| Alloxan | — | 0.5 |
| OPEA | 1.0 | 1.0 |
| Deionized water | to 100 | to 100 |

Example 13

Color development of Samples 38 to 40 were compared to similar compositions formulated with glycine and DHA and DHA and no adjuvant. Color development was assessed in a manner similar to the one described in Example 7. Samples 38 to 40 and compositions with glycine as the adjuvant performed (i.e., darkened) to a greater extent and about 33% faster than compositions free of adjuvant. The results, surprisingly, indicate that OPEA and glycine perform essentially the same in illustrative end use compositions with DHA. The results, surprisingly, further show use of OPEA is not limited to one sunless tanning agent.

What is claimed is:

1. A composition comprising:
   a) a sunless tanning agent; and
   b) an adjuvant for the sunless tanning agent, said adjuvant comprising o-phosphorylethanolamine.

2. The composition according to claim 1 wherein the sunless tanning agent is dihydroxyacetone, melanin, mahakanni (eclipta alba), methyl glyoxal, erythrulose, alloxan, 2,3-dihydroxysuccindialdehyde or a mixture thereof.

3. The composition according to claim 1 wherein the sunless tanning agent is alloxan, dihydroxyacetone, erythrulose or a mixture thereof.

4. The composition according to claim 1 wherein the sunless tanning agent is dihydroxyacetone.

5. The composition according to claim 1 wherein the composition further comprises a cosmetically acceptable carrier.

6. The composition according to claim 1 wherein the cosmetically acceptable carrier is an oil-in-water emulsion.

7. The composition according to claim 1 wherein the composition further comprises a cationic ammonium compound.

8. The composition according to claim 7 wherein the cationic ammonium compound is 1,2-dihydroxypropyltrimoniumn chloride.

9. The composition according to claim 1 wherein the sunless tanning agent makes up from about 0.025 to about 35% by weight of the composition.

10. The composition according to claim 1 wherein the adjuvant makes up from about 0.025 to about 35% by weight of the composition.

11. The composition according to claim 1 wherein the composition has a pH from about 3 to about 4.75.

12. The composition according to claim 1 wherein the composition is in a dual compartment package comprising at least two compartments.

13. The composition according to claim 12 wherein the first compartment comprises sunless tanning agent and the second compartment comprises adjuvant.

14. A method for imparting a sunless tan comprising the step of topically applying to skin the composition of claim 1.

* * * * *